(12) United States Patent
McKeever et al.

(10) Patent No.: US 9,388,203 B2
(45) Date of Patent: Jul. 12, 2016

(54) PHARMACEUTICAL PROCESS AND INTERMEDIATES

(71) Applicants: Benedict McKeever, Macclesfield (GB); Louis Joseph Diorazio, Macclesfield (GB); Martin Francis Jones, Macclesfield (GB); Leigh Ferris, Macclesfield (GB); Sophie Laure Marie Janbon, Macclesfield (GB); Pawel Stanislaw Siedlecki, Macclesfield (GB); Gwydion Huw Churchill, Macclesfield (GB); Peter Alan Crafts, Aberdeenshire (GB)

(72) Inventors: Benedict McKeever, Macclesfield (GB); Louis Joseph Diorazio, Macclesfield (GB); Martin Francis Jones, Macclesfield (GB); Leigh Ferris, Macclesfield (GB); Sophie Laure Marie Janbon, Macclesfield (GB); Pawel Stanislaw Siedlecki, Macclesfield (GB); Gwydion Huw Churchill, Macclesfield (GB); Peter Alan Crafts, Aberdeenshire (GB)

( * ) Notice: Subject to any disclaimer, the term of this patent is extended or adjusted under 35 U.S.C. 154(b) by 0 days.

(21) Appl. No.: 14/576,544

(22) Filed: Dec. 19, 2014

(65) Prior Publication Data

US 2015/0175639 A1   Jun. 25, 2015

Related U.S. Application Data

(60) Provisional application No. 61/919,671, filed on Dec. 20, 2013.

(51) Int. Cl.
*C07F 9/6561* (2006.01)
*C07D 498/04* (2006.01)

(52) U.S. Cl.
CPC .................................. *C07F 9/6561* (2013.01)

(58) Field of Classification Search
CPC ............................ C07F 9/6561; C07D 498/04
USPC .......................................................... 544/105
See application file for complete search history.

(56) References Cited

U.S. PATENT DOCUMENTS 8,299,242 B2 * 10/2012 Felfer et al. ................... 544/105

FOREIGN PATENT DOCUMENTS

WO   2011/002999 A1   1/2011

* cited by examiner

*Primary Examiner* — Kahsay Habte
(74) *Attorney, Agent, or Firm* — McDonnell Boehnen Hulbert & Berghoff LLP

(57) ABSTRACT

The present disclosure provides for processes and intermediates in the large-scale manufacture of the compound of formula (I) or hydrates thereof.

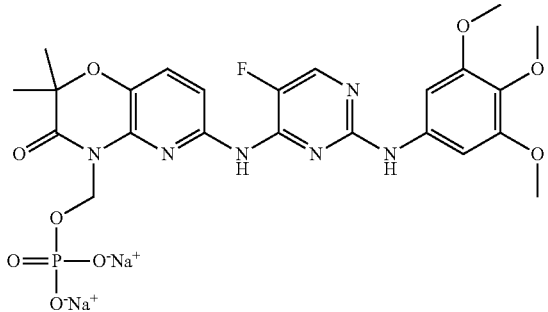

17 Claims, No Drawings

PHARMACEUTICAL PROCESS AND INTERMEDIATES

This application is a nonprovisional application which claims priority to U.S. Provisional Patent Application Ser. No. 61/919,671 filed on Dec. 20, 2013, the disclosure of which is incorporated herein by reference.

BACKGROUND OF THE INVENTION

1. Field of the Invention

The present invention relates to the large-scale manufacture of pharmaceutical compounds, in particular the large-scale manufacture of 2,4-pyrimidinediamines and intermediates used therein.

2. Background of the Invention

International patent application WO 2005/016893 discloses 2,4-pyrimidinediamine compounds, and pharmaceutically acceptable salts thereof and processes thereto, which are useful in the treatment and prevention of various diseases.

International patent application WO 2006/078846 discloses prodrugs of 2,4-pyrimidinediamine compounds and processes thereto.

International patent application WO 2011/002999 discloses a process for preparing a 2,4-pyrimidinediamine compound of formula (I):

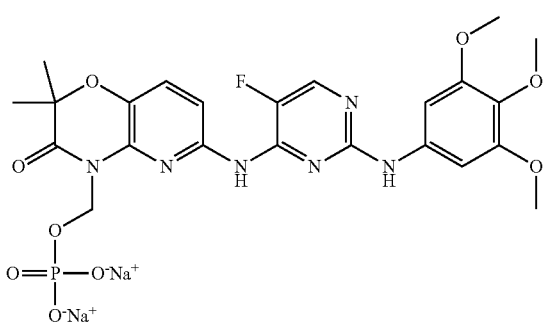

(I)

The compound of formula (I) is being developed as an active pharmaceutical compound.

SUMMARY OF THE INVENTION

Appropriate methods for the cost-effective, efficient and environmentally sensitive manufacture of the compound of formula (I) are desirable. It is also desirable to utilize manufacturing conditions that reduce product degradation and improve reaction selectivity. The present invention provides processes for the large-scale manufacture of a compound of formula (I) as well as hydrates (such as hexahydrates) thereof.

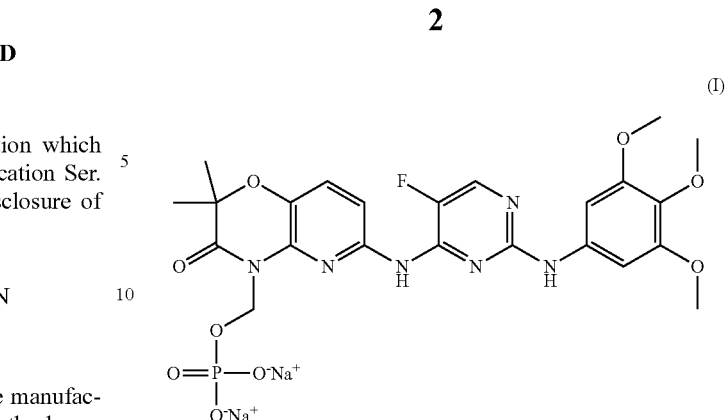

(I)

In a first aspect of the invention, there is provided a process for preparing a compound of formula (I) or hydrate thereof which comprises:

(a) contacting an amide solvate of the compound of formula (II) with an amine under conditions suitable for forming an amine salt of the compound of formula (II);

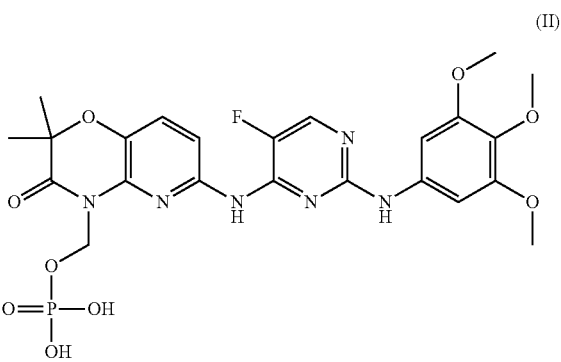

(II)

and (b) contacting the amine salt with a reagent comprising sodium ions under conditions suitable for forming the compound of formula (I) or hydrate thereof.

In an embodiment of the invention, the compound of formula (I) produced by this method is a hydrate. In a particular embodiment the compound of formula (I) produced by this method is a hexahydrate.

In some embodiments, the amide component of the amide solvate of the compound of formula (II) is $R^{30}CON(R^2)_2$ where each $R^2$ is independently —H or $C_{1-4}$ alkyl, or both $R^2$ groups together with the nitrogen to which they are attached form a 4 to 6-membered heterocyclic ring, and $R^{30}$ is —H or $C_{1-4}$ alkyl; or $R^{30}$ and one of the $R^2$ groups together with the nitrogen to which they are attached, respectively, combine to form a 4 to 6-membered heterocyclic ring, and the other $R_2$ group is independently —H or $C_{1-4}$ alkyl.

In some embodiments, the amide component is selected from N,N-di-($C_{1-4}$ alkyl)-formamide, N,N-di-($C_{1-4}$ alkyl)-acetamide, N—$C_{1-6}$ alkyl-pyrrolidinone or N—$C_{1-6}$ alkyl-piperidinone.

In a yet further embodiments, the amide component is N,N-dimethylformamide (DMF).

In a particular embodiment, the amide solvate is of formula (III):

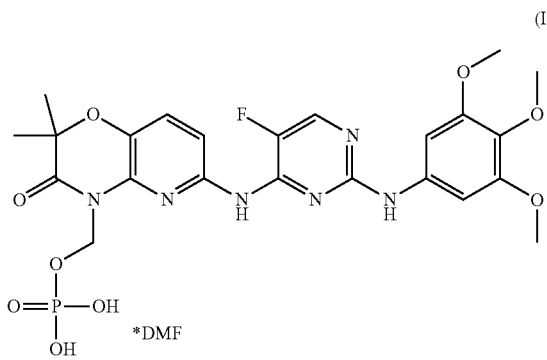

(III)

*DMF

In a still further embodiment, the amine component of the amine salt of the compound of formula (II) is $N(R^{40})_3$ where each $R^{40}$ is independently —H or $C_{1-12}$alkyl, or two $R^{40}$ groups together with the nitrogen to which they are attached form a 4 to 6-membered heterocyclic ring and the remaining $R^{40}$ group is —H or $C_{1-12}$alkyl.

In a yet further embodiment, the amine component of the amine salt of the compound of formula (II) is $N(R^{40})_3$ where each $R^{40}$ is independently $C_{1-12}$ alkyl, or two $R^{40}$ groups together with the nitrogen to which they are attached form a 4 to 6-membered heterocyclic ring and the remaining $R^{40}$ group is $C_{1-12}$ alkyl.

In a further embodiment the amine component is selected from $N(C_{1-6}$ alkyl$)_3$, N-methyl morpholine or N-methyl piperidine.

In a still further embodiment, the amine component is $N(C_{1-6}$ alkyl$)_3$ such as trimethylamine, dimethylethylamine, triethylamine, tripropylamine, tributylamine or di-isopropylethylamine.

In a further embodiment, the amine component is triethylamine.

In a further embodiment, the amine salt of the compound of formula (II) is the triethylammonium salt. In a still further embodiment, the stoichiometric ratio of triethylamine to the compound of formula (II) is between 0.5:1 and 2.5:1, for example between 1.5:1 and 2.5:1, such as about 2:1. In a yet further embodiment, the amine salt is the bis(triethylammonium) salt of the compound of formula (II) (the compound of formula (IV)):

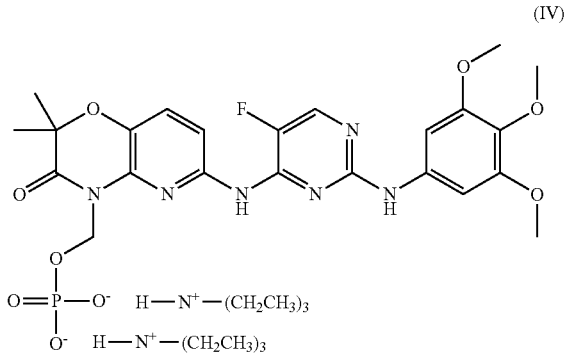

(IV)

In a further embodiment, the conditions suitable for forming an amine salt of the compound of formula (II) comprises combining a solution of the amine in a polar solvent and water with the amide solvate of the compound of formula (II).

In a further embodiment, the conditions suitable for forming an amine salt of the compound of formula (II) comprise:
(i) combining a solution of the amine in a polar solvent and water with the amide solvate of the compound of formula (II); and
(ii) filtering the reaction mixture.

In a still further embodiment, the polar solvent is selected from an alcohol, acetone, acetonitrile and dimethylsulfoxide. In a yet further embodiment the polar solvent is an alcohol, such as isopropanol.

In a further embodiment, the formation of the amine salt is carried out at a temperature not exceeding 70° C., for example from about 0° C. and not exceeding 60° C., 50° C., 40° C., 30° C., 20° C. or 10° C., such as from about 10° C. to about 30° C. In a still further embodiment, the formation of the amine salt is carried out at ambient temperature.

In a yet further embodiment, the solution of the amine in a polar solvent and water is added to the amide solvate.

In a further embodiment, the conditions suitable for forming the compound of formula (I) or hydrate thereof comprises combining a solution of the reagent comprising sodium ions in a polar solvent and water with the solution of the amine salt of the compound of formula (II) as obtained from the preceding step.

In a still further embodiment, the polar solvent is selected from an alcohol, acetone, acetonitrile and dimethylsulfoxide. In a yet further embodiment the polar solvent is an alcohol, such as isopropanol. In a still further embodiment, the polar solvent is the same as the polar solvent used in the preceding step.

In a further embodiment, the reagent comprising sodium ions is selected from sodium chloride, sodium acetate, sodium carbonate, sodium sulphate or sodium 2-ethylhexanoate, for example sodium chloride or sodium ethylhexanoate, such as sodium 2-ethylhexanoate.

In a further embodiment, the reagent comprising sodium ions is added to the solution of the amine salt.

In a further embodiment, the formation of the compound of formula (I) or hydrate thereof is carried out at a temperature not exceeding 70° C., for example not exceeding 60° C., 50° C., 40° C., 30° C., 20° C. or 10° C. In a still further embodiment, the formation is carried out at a temperature not exceeding 40° C.

In a yet further embodiment, the solution of the amine salt is warmed to the required reaction temperature prior to the addition of the reagent comprising sodium ions.

In a still further embodiment, the combined solution of the reagent comprising sodium ions with the solution of the amine salt of the compound of formula (II) further comprises a seed of the compound of formula (I) or hydrate thereof.

In a further embodiment, a proportion of the reagent comprising sodium ions (for example less than 50%, such as less than 40%, 30%, 20%, 10% or 5%, for example less than 5%) and a seed of the compound of formula (I) or hydrate thereof is added to the solution of the amine salt of the compound of formula (II). The reaction mixture is then held for a period of time (for example at least 2 hours, such as at least 3 hours, 4 hours, 5 hours, 12 hours or 24 hours) before the remaining reagent comprising sodium ions is added.

In a further embodiment, the reagent comprising sodium ions is added over an extended period of time (for example at least 2 hours, such as at least 3 hours, 4 hours, 5 hours, 12 hours or 24 hours).

In a further embodiment, the reaction mixture is cooled to a temperature not exceeding 30° C., for example not exceeding 20° C. or 10° C., prior to filtration. In a still further embodiment, the reaction mixture is cooled to ambient temperature prior to filtration.

In a further embodiment, the conditions suitable for forming the compound of formula (I) or hydrate thereof further comprise washing the reaction mixture with a polar solvent and water after filtration.

This process of converting an amide solvate of a compound of formula (II) into a compound of formula (I) or hydrate thereof provides a number of advantages over previously described processes and is more suited to large-scale manufacture.

This process improves the product yield compared to previous disclosures from a product yield of 77% for this conversion as described in WO 2011/002999, to a product yield of greater than 90%.

This process reduces the overall process volume as described previously, such as, for example, enabling use of 8 relative volumes compared to 15 relative volumes. This is a factor in the improved product yield. A reduction in overall volume also provides economic and environmental advantages.

The skilled person will be aware that in the manufacture of active pharmaceutical compounds, the incorporation of a filtration step for solutions of all materials used in the final process step is a requirement to eliminate particulate matter from the isolation process and from the final product. The amine salt (a triethylammonium salt, such as the bis(triethylammonium) salt) generated in this process can be prepared and the resulting solution filtered at ambient temperature without significant undesired product degradation. The amine salt can also be prepared and the resulting solution filtered at ambient temperature without significant undesired premature precipitation of solids. Previously described processes required a filtration step at elevated temperatures (e.g., in excess of 80° C.) in order to ensure complete solution. Significant product degradation may occur under such conditions, thereby requiring that such procedures are carried out rapidly. This may lead to premature product precipitation and/or poor control of product crystallization and may lead to difficulties in adapting the processes to a very large scale.

Furthermore, the additional step of forming an amine salt allows for the formation of a stable solution. The formation of a stable solution enables the use of a seed of the compound of formula (I) or hydrate thereof. This allows for improved control of product crystallization and improved control of the hydration of the final product solid form. Previously described processes did not readily allow the use of a controlled seeded crystallization.

This process further utilizes sodium 2-ethylhexanoate as the reagent comprising sodium ions. This reagent is highly soluble in organic solvents and can be added in relatively high concentration whilst minimizing the risk of precipitation of unwanted impurities. This is a factor in the improved product yield. Further, the weakly basic nature of this reagent allows high concentrations to be added without significantly affecting the overall pH of the process system. This allows improved control of product formation without degradation. Previously described processes required the use of sodium hydroxide which did not readily provide the desired control of pH when added in large quantities, the resulting increase in pH leading to increased product degradation and reduced product yield.

The conditions selected to carry out the formation of the compound of formula (I) or hydrate thereof as described in this process allows for the reaction to be carried out at a temperature less than or equal to 40° C. Previously described processes carried out this step at temperatures in excess of 60° C. The present process significantly reduces product degradation and hence improve product yield (from a degradation rate of over 10% after 3 hours for previously described processes, to a degradation rate of about 1% after 24 hours).

Furthermore, the introduction of an amine salt and the use of sodium 2-ethylhexanoate in this process instead of sodium hydroxide reduces the risk of precipitation of an undesired salt, for example the monosodium salt. The solubility of the amine salt is such that any potential intermediate salts thereof is significantly more soluble than the desired disodium salt of formula (I) or hydrate thereof. Previously described processes would have passed through an intermediate monosodium salt species which led to an increased risk of unwanted precipitation of the monosodium salt. The present process maintains a consistent pH level at which the monosodium salt species is unlikely to form.

In a second aspect of the invention, there is provided a compound which is a triethylammonium salt of the compound of formula (II). In an embodiment, there is provided a triethylammonium salt of the compound of formula (II) wherein the stoichiometric ratio of triethylamine to the compound of formula (II) is between 0.5:1 and 2.5:1, for example between 1.5:1 and 2.5:1, such as about 2:1. In a still further embodiment, there is provided the bis(triethylammonium) salt of the compound of formula (II) (a compound of formula (IV)):

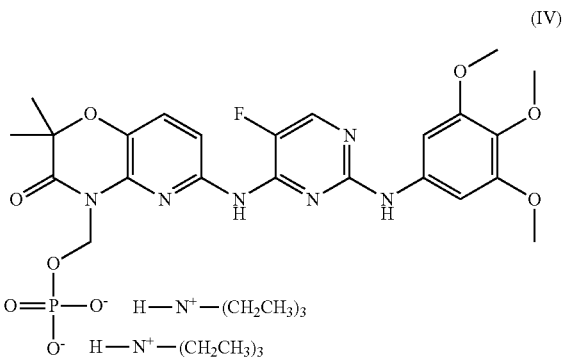

(IV)

In a further embodiment, there is provided a compound of formula (IV) for use as an intermediate in the manufacture of a compound of formula (I) or hydrate thereof.

A process for preparing an amide solvate of a compound of formula (II) is described in WO 2011/002999. Specifically, the amide solvate is prepared from the acetic acid solvate of formula (V):

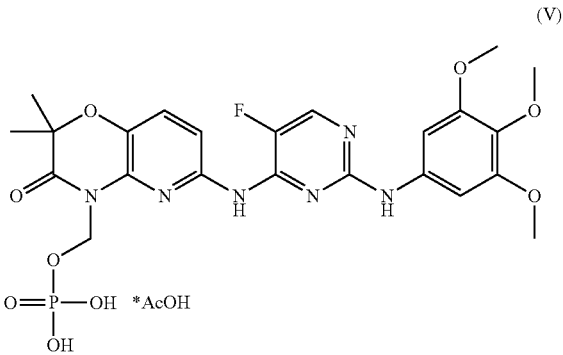

(V)

In a further aspect of the invention, there is provided a process for preparing an amide solvate of a compound of formula (II) comprising contacting a compound of formula (V) with an amide at a temperature exceeding 60° C., such as 65° C., for example from about 65° C. to about 100° C., such as to about 85° C. or from about 60° C. to about 75° C.

In an embodiment, the amide is $R^{30}CON(R^2)_2$ where each $R^2$ is independently —H or $C_{1-4}$ alkyl, or both $R^2$ groups together with the nitrogen to which they are attached form a 4 to 6-membered heterocyclic ring, and $R^{30}$ is —H or $C_{1-4}$ alkyl; or $R^{30}$ and one of the $R^2$ groups together with the nitrogen to which they are attached, respectively, combine to form a 4 to 6-membered heterocyclic ring, and the other $R_2$ group is independently —H or $C_{1-4}$ alkyl.

In a further embodiment, the amide is selected from the group consisting of a N,N-di-($C_{1-4}$ alkyl)-formamide, N,N-di-($C_{1-4}$ alkyl)-acetamide, N—$C_{1-6}$ alkyl-pyrrolidinone and N—$C_{1-6}$ alkyl-piperidinone.

In a yet further embodiment, the amide is N,N-dimethylformamide (DMF).

In a further embodiment, the amide solvate is of formula (III):

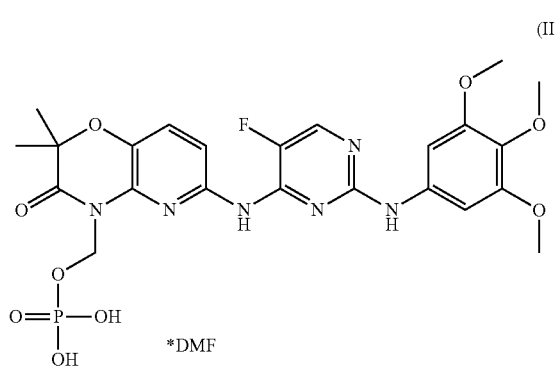

(III)

*DMF

In a still further embodiment, the reaction mixture is heated to a temperature exceeding 60° C., such as 65° C., maintained at that temperature for at least 10 minutes (for example at least 30 minutes, such as at least 1 hour) and thereafter cooled to a temperature not exceeding 50° C. (for example not exceeding 40° C., such as not exceeding 30° C.). In a further embodiment the reaction mixture is cooled over a period of at least 1 hour (for example at least 2 hours, such as at least 4 hours) and thereafter heated again to a temperature not exceeding 60° C. In a still further embodiment the reaction mixture is heated to that temperature over a period of at least 1 hour, such as 2 hours. In a still further embodiment, the reaction mixture is cooled to ambient temperature over a period of at least 1 hour (for example at least 4 hours, such as at least 8 hours).

In a further embodiment, the reaction mixture further comprises a seed of the amide solvate of a compound of formula (II), for example a seed of the amide solvate of formula (III).

This process of preparing an amide solvate of a compound of formula (II) provides a number of advantages over previously described processes and is more suited to large-scale manufacture.

The process is carried out at a higher temperature than previously disclosed (exceeding 60° C. compared to about 50° C.). The process further utilizes a temperature cycling and controlled cooling profile. These, together or independently, provide both improved product physical form and improved filterability, hence improving the process from a large-scale manufacturing perspective.

In a further aspect of the invention, there is provided a process for preparing a compound of formula (V) comprising contacting a compound of formula (VI) with acetic acid and water under conditions suitable for forming the compound of formula (V):

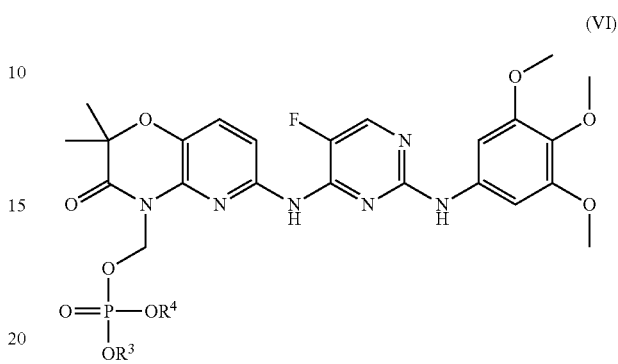

(VI)

wherein $R^3$ and $R^4$ are each independently $C_{1-6}$ alkyl.

In an embodiment, $R^3$ and $R^4$ are both tert-butyl.

In a still further embodiment, the conditions suitable for forming the compound of formula (V) comprises combining a solution of a compound of formula (VI) in a polar solvent with a solution of acetic acid and water.

In a further embodiment, the polar solvent is selected from methyl tert-butyl ether (MTBE) or isopropyl acetate, such as isopropyl acetate.

In a further embodiment, the solution of a compound of formula (VI) in a polar solvent is added to the solution of acetic acid and water. In a yet further embodiment, the addition of the solution of a compound of formula (VI) is carried out over a period of several hours, for example up to 6 hours, such as up to about 5 hours.

In a further embodiment, the combined solution is heated to 50-90° C. In a yet further embodiment, the solution is heated to 70° C.

In a further embodiment, the filtering is carried out at an elevated temperature, for example about 50° C.

In a still further embodiment, the solution of acetic acid and water further comprises a seed of the compound of formula (V).

In a further embodiment, the conditions suitable for forming the compound of formula (V) further comprise washing the reaction mixture with a polar solvent.

In another embodiment, the compound of formula (VI) may be added directly in solid form to the solution of acetic acid and water.

This process of converting a compound of formula (VI) into an acetic acid solvate of formula (V) provides a number of advantages over previously described processes and is more suited to large-scale manufacture.

This process involves the addition of a seed of the compound of formula (V). It further involves the controlled addition of the solution of a compound of formula (VI) over a period of several hours. This significantly improves the product filtration rate. This allows for a significantly easier filtering process (for example, a filtration rate of 0.46 h/kg for previously described processes, compared to a filtration rate of 0.21 h/kg for the present process).

Furthermore, this process discloses filtering of the reaction mixture at an elevated temperature. This also improves the ease of filtering.

An inefficient filtering step can be a significant problem in the large-scale manufacture of pharmaceutical products. The present disclosure therefore provides significant economic and environmental advantages over processes previously described.

In a further aspect of the present invention there is provided a process for preparing a compound of formula (VI) comprising contacting a compound of formula (VII):

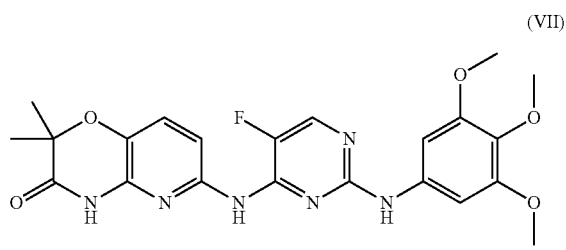

(VII)

with a compound of formula (VIII):

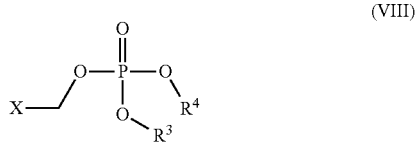

(VIII)

in the presence of a tetra-alkylammonium salt (such as tetra-n-butylammonium chloride (TBAC)) under conditions suitable for forming a compound of formula (VI), and wherein $R^3$ and $R^4$ are each independently $C_{1-6}$ alkyl, and X is halogen.

In an embodiment, the compound of formula (VIII) is di-tert-butyl chloromethyl phosphate (IX):

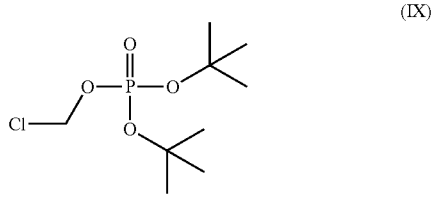

(IX)

In a still further embodiment, the conditions sufficient to produce the compound of formula (VI) comprise:

(i) combining the compound of formula (VII) with the compound of formula (VIII) with tetra-n-butylammonium chloride and a base in a polar solvent; and (ii) washing the product obtained from (i) with water.

In a further embodiment, the base is an inorganic base, for example caesium carbonate, potassium carbonate or potassium tert-butoxide, such as potassium carbonate.

In a yet further embodiment, the polar solvent comprises N,N-dimethylacetamide (DMAC), 1,3-dimethyl-2-imidazolidinone (DMI), N,N-dimethylformamide, sulfolane, methyl tert-butyl ether, 2-methyltetrahydrofuran, or isopropyl acetate (IPAC), or a mixture thereof.

In a further embodiment, the polar solvent comprises a mixture of N,N-dimethylacetamide (DMAC) and isopropyl acetate (IPAC).

In a further embodiment, the reaction in step (i) is carried out at a temperature of between 20-50° C., such as about 40° C.

In a further embodiment, a solution of the compound of formula (VIII) in a polar solvent (such as isopropyl acetate) is added to a solution of the compound of formula (VII), a tetra-alkylammonium salt (such as tetra-n-butylammonium chloride) and a base (such as potassium carbonate) in a polar solvent (such as N,N-dimethylacetamide).

In a further embodiment, after completion of the reaction in step (i), the reaction mixture is cooled (such as to about 5° C.), further polar solvent (such as isopropyl acetate) added and the reaction mixture washed with water. In a still further embodiment, the temperature of the solution during work-up is maintained at less than 25° C.

This process of converting a compound of formula (VIII) into a compound of formula (VI) provides a number of advantages over previously described processes and is more suited to large-scale manufacture. In particular, the alkylation reaction may be difficult to control, in particular the selectivity between the desired amide N-alkylation and the undesired amide O-alkylation. This process improves reaction selectivity (for example by improving the N:O selectivity from about 6:1 to about 14:1 compared to previously disclosed processes). This process further improves overall product yield on a manufacturing scale (for example by about 5-10% over previously disclosed processes).

This process discloses the use of tetra-n-butylammonium chloride. Without wishing to be bound by theory, it is believed that the introduction of this reagent has a subtle effect on the solubility of the base used and on the subsequent solubility and reactivity of the anion of the compound of formula (VII), which leads to an improvement in both the rate and the selectivity of the reaction. Previously disclosed processes do not utilize tetra-n-butylammonium chloride and therefore do not have the desired rate or selectivity profile.

Furthermore, this process introduces isopropyl acetate as additional solvent, which was not disclosed as solvent in previous processes. The introduction of a mixed N,N-dimethylacetamide/isopropyl acetate solvent allows for a reduced total process volume, as a lower N,N-dimethylacetamide burden reduces the volume of water required during reaction work-up. In addition, isopropyl acetate can be used as both a reaction solvent and an extraction solvent, again reducing the overall process volume (for example from 23 relative volumes of solvent for previously described processes, to 18 relative volumes of solvent for the present process). Further, the introduction of isopropyl acetate leads to a simplified work-up procedure, consisting of a single wash, rather than the multiple washes previously described.

In a further aspect of the present invention there is provided a process for preparing di-tert-butyl chloromethyl phosphate (IX) comprising contacting a mixture of potassium di-tert-butylphosphate, tetra-n-butylammonium hydrogen sulphate (TBAHS) and sodium hydrogen carbonate in a polar solvent and water with chloromethylchlorosulphate.

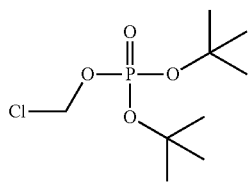

(IX)

In an embodiment, the polar solvent is selected from 2-methyltetrahydrofuran, methyl tert-butyl ether and isopropyl acetate, such as isopropyl acetate.

In a further embodiment, the solution comprises a mixture of water and isopropyl acetate.

In a further embodiment, the solution is heated to a temperature exceeding ambient temperature (such as exceeding 30° C., for example exceeding 35° C.).

This process of preparing di-tert-butyl chloromethyl phosphate (IX) provides a number of advantages over previously described processes. In particular, the previous process required the addition of DMAC to control the decomposition of di-tert-butyl chloromethyl phosphate (IX). This process resulted in a difficult distillation to remove residual solvents from the DMAC solution prior to use in the subsequent process. The use of isopropyl acetate as solvent removes the need to use DMAC and allows for a much more straightforward distillation process, more suited to large-scale manufacture.

In a further aspect of the present invention, there is provided a process for preparing a compound of formula (I) or hydrate thereof:

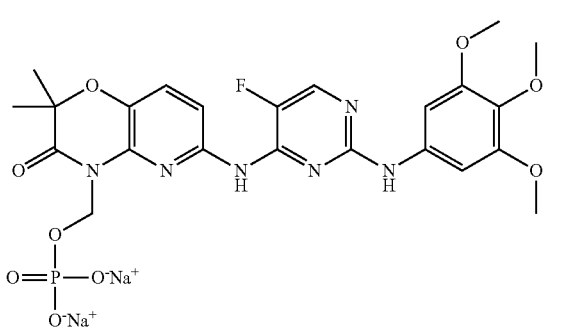

(I)

comprising:
(a) contacting a compound of formula (VI):

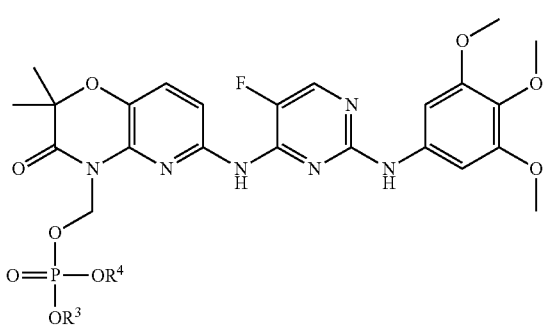

(VI)

wherein $R^3$ and $R^4$ are as previously described;
with acetic acid and water under conditions suitable for forming the compound of formula (V):

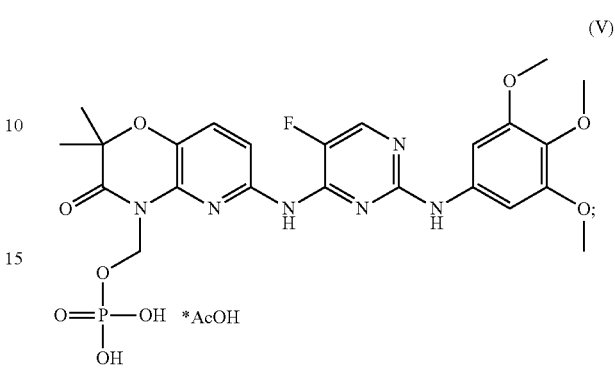

(V)

contacting the compound of formula (V) with an amide under conditions suitable for forming an amide solvate of the compound of formula (II):

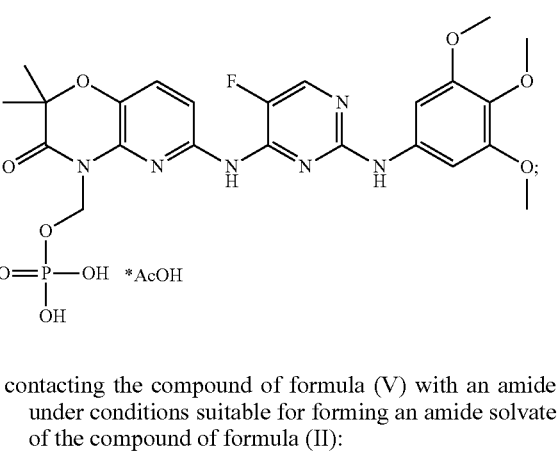

(II)

(b) contacting the amide solvate of the compound of formula (II) with an amine under conditions suitable for forming an amine salt of the compound of formula (II); and (c) contacting the amine salt of the compound of formula (II) with a reagent comprising sodium ions under conditions suitable for forming the compound of formula (I) or hydrate thereof.

In an embodiment, the compound of formula (I) produced by this method is a hydrate, such as a hexahydrate. Each of the embodiments described with respect to a particular process step above can be performed independently or combined with one or more embodiments for other process steps. For example, in the process above, or independently, the amide in (b) can be $R^{30}CON(R^2)_2$, such as N,N-di-($C_{1-4}$ alkyl)-formamide, N,N-di-($C_{1-4}$ alkyl)-acetamide, N—$C_{1-6}$ alkyl-pyrrolidinone, N—$C_{1-6}$ alkyl-piperidinone or a combination thereof. Independently, the amine recited in (c) above can be $N(R^{40})_3$, such as $N(C_{1-6}$ alkyl$)_3$, N-methyl morpholine or N-methyl piperidine, or more particularly, selected from trimethylamine, dimethylethylamine, triethylamine, tripropylamine, tributylamine, di-isopropylethylamine and combinations thereof. Similarly and independently the reagent comprising sodium ions in (d) is selected from sodium chloride, sodium acetate, sodium carbonate, sodium sulphate, sodium 2-ethylhexanoate and combinations thereof.

DETAILED DESCRIPTION OF THE INVENTION

"Alkyl" refers to monovalent saturated aliphatic hydrocarbyl groups having, unless expressly stated otherwise, from 1 to 8 carbon atoms, such as, 1 to 6 carbon atoms or 1 to 4 carbon atoms. This term includes, by way of example, linear and branched hydrocarbyl groups such as methyl, ethyl, n-propyl, isopropyl, n-butyl, isobutyl, sec-butyl, tert-butyl, n-pentyl and neopentyl. Also by way of example, a methyl group, an ethyl group, an n-propyl group, an isopropyl group, an n-butyl group, an iso-butyl group, a sec-butyl group and a tert-butyl group are all represented by the term $C_{1-4}$ alkyl. Likewise terms indicating larger numerical ranges of carbon atoms (for example $C_{1-6}$ alkyl) are representative of any linear or branched hydrocarbyl falling within the numerical range.

"Ambient temperature" refers to a temperature of between 15° C. to about 25° C., for example between 18° C. to 22° C., such as about 20° C.

"Base" refers to a substance that can accept protons. Examples of bases include, but are not limited to, inorganic bases, for example carbonates (such as cesium carbonate, sodium carbonate, sodium bicarbonate, potassium carbonate) and hydroxides (such as sodium hydroxide, potassium hydroxide or lithium hydroxide), and organic bases, for example nitrogen-containing organic bases (such as ammonia, methylamine, dimethylamine, ethylamine, diethylamine, dimethylethylamine, triethylamine or di-isopropylethylamine).

"Halogen" refers to fluoro, chloro, bromo or iodo.

"Heterocyclic" means a C-linked or N-linked, 4 to 6-membered, monocyclic saturated ring system containing 1-3 heteroatoms independently selected from N, S and O. By way of example, such heterocyclic rings include morpholinyl, piperidinyl, piperazinyl, and pyrrolidinyl rings, including N-alkylated version of such rings, such as N-methyl morpholinyl and N-methyl piperidinyl.

"Solvate" refers to a complex formed by combination of at least one solvent molecule with at least one molecule or ion of the solute. One of ordinary skill in the art will appreciate that the stoichiometry of the solvent to the solute in a solvate may be greater than one, equal to one, or less than one. The solvent can be an organic compound, an inorganic compound, or a mixture of both. Some examples of solvents include, but are not limited to, acetic acid, N,N-di-($C_{1-4}$ alkyl)-formamide, N,N-di-($C_{1-4}$ alkyl)-acetamide, N—$C_{1-6}$ alkyl-pyrrolidinone, N—$C_{1-6}$ alkyl-piperidinone, N,N-dimethylformamide and water. When used herein, the term "solvate" is not intended to restrict the solvate compounds described herein to any particular sort of bonding (such as ionic or covalent bonds).

In a salt, proton transfer occurs between the compound of formula (II) and the counter ion of the salt (such as triethylamine). The skilled person will be aware that in some cases proton transfer may not be complete and the solid is not therefore a true salt. In such cases the compound of formula (II) and the "co-former" molecules in the solid primarily interact through non-ionic forces such as hydrogen bonding. It is accepted that proton transfer is a continuum, and can change with temperature, and therefore the point at which a salt is better described as a co-crystal can be somewhat subjective. The compound of formula (II) may therefore form a mixture of salt and co-crystal forms and it is to be understood that the present invention encompasses the salt forms, co-crystal forms and salt/co-crystal mixtures, as well as any solvates (including hydrates) thereof.

The synthesis of di-tert-butyl chloromethyl phosphate (IX) is illustrated in Scheme I below.

Scheme I

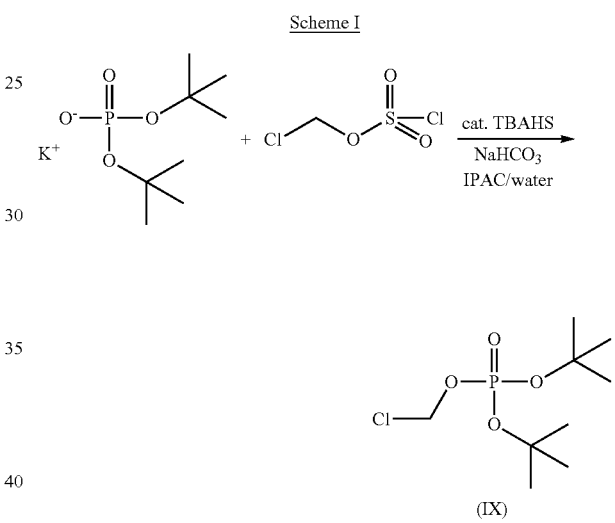

The synthesis of the compound of formula (VI) wherein $R^3$ and $R^4$ are both tert-butyl (formula (X)) from the compound of formula (VII) is illustrated in Scheme II below.

Scheme II

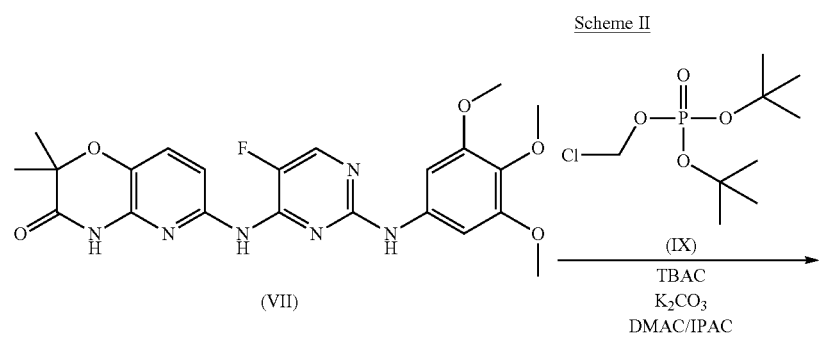

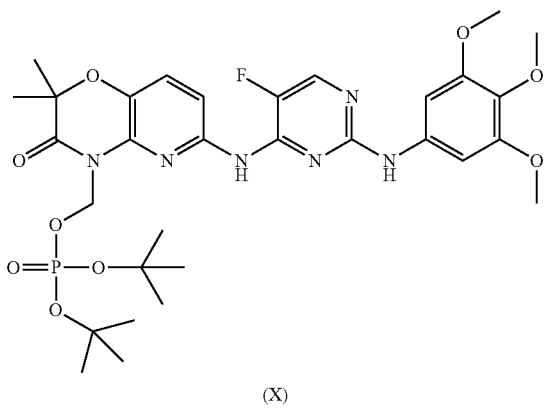

(X)

The synthesis of the compound of formula (V) from the compound of formula (X) is illustrated in Scheme III below.

Scheme III

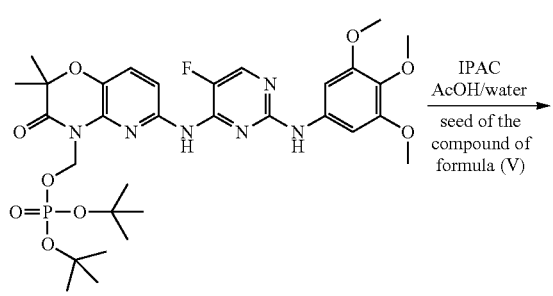

(X)

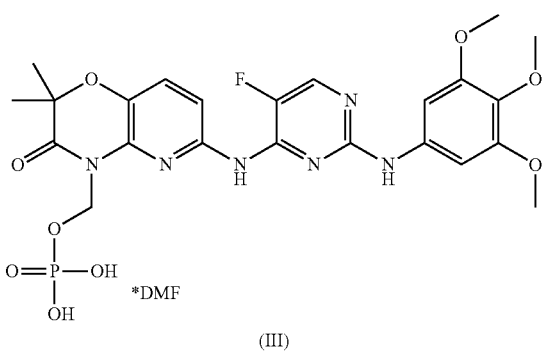

(V)

The synthesis of the compound of formula (III) from the compound of formula (V) is illustrated in Scheme IV below.

Scheme IV

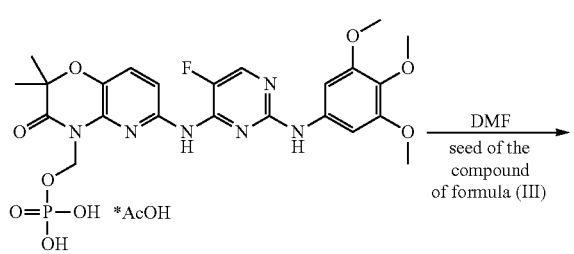

(V)

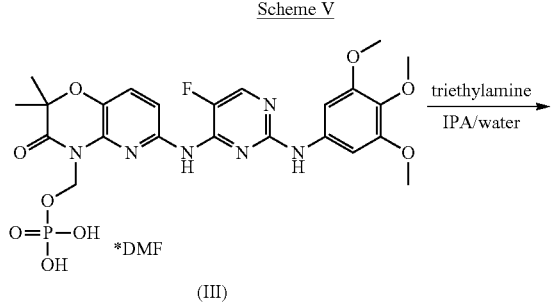

(III)

The synthesis of the bis(triethylammonium) salt of the compound of formula (II) (the compound of formula (IV)) is illustrated in Scheme V below.

Scheme V

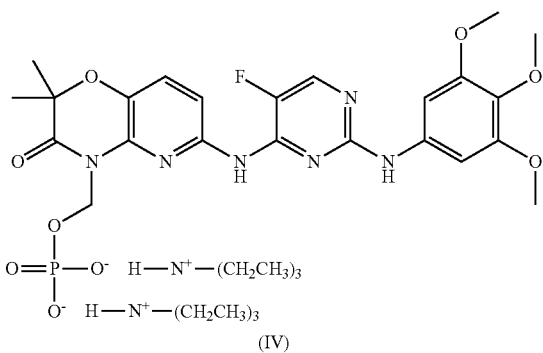

(III)

(IV)

The synthesis of the compound of formula (I) or hydrate thereof from the compound of formula (IV) is illustrated in Scheme VI below.

Scheme VI

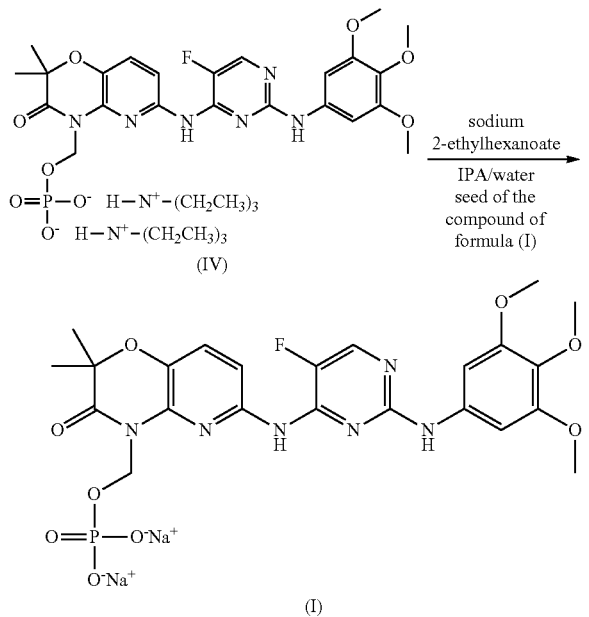

(I)

EXAMPLES

The invention is further understood by reference to the following examples, which are intended to be purely exemplary of certain aspects of the invention and are not intended to limit the scope.

In the examples below as well as throughout the specification, the following abbreviations have the following meanings. If not defined, the terms have their generally accepted meanings.

AcOH=acetic acid
DMAC=N,N-dimethylacetamide
DMF=N,N-dimethylformamide
DMI=1,3-dimethyl-2-imidazolidinone
DMSO=dimethylsulfoxide
g=gram
IPA=isopropanol
IPAC=isopropyl acetate
kg=kilogram
L=liter
mbar=millibar
ml=milliliter
mol eq=molar equivalent
MTBE=methyl tert-butyl ether
TBAC=tetra-n-butylammonium chloride
TBAHS=tetra-n-butylammonium hydrogen sulphate
w/v=weight/volume
w/w=weight/weight General Procedures Proton ($^1$H) and carbon ($^{13}$C) nuclear magnetic resonance (NMR) spectra were acquired using Bruker Avance 400 spectrometer at 300 K. Samples were prepared as solutions in $d_6$-DMSO ($d_6$-dimethyl sulfoxide) containing trimethylsilane (TMS), or $d_4$-MeOD ($d_4$-methanol). NMR data is reported as a list of chemical shifts (δ, in ppm) with a description of each signal, using standard abbreviations (s=singlet, d=doublet, m=multiplet, t=triplet, q=quartet, br=broad, etc.). Spectra were referenced $d_6$-DMSO (δ=2.50 ppm) or $d_4$-MeOD (δ=3.30 ppm). J-Coupling constants are listed, where measured, in the descriptions of the resonances. Slight variation of chemical shifts and J-coupling constants may occur, as is well known in the art, as a result of variations in sample preparation, such as analyte concentration variations.

Mass spectrometry data was obtained using a Bruker micrOTOF-Q quadrupole time-of-flight mass spectrometer. Samples were analyzed using positive ion electrospray ionization. Accurate mass measurement was used to determine the elemental formula of the resulting ions.

Large scale reactions were carried out in glass-lined steel reactors fitted with heat transfer jackets and serviced with appropriate ancillary equipment. Standard laboratory glassware and equipment was used for smaller scale processes. Starting materials, solvents and reagents were purchased commercially and used as supplied.

Example 1

Preparation of disodium [6-[[5-fluoro-2-(3,4,5-trimethoxyanilino)pyrimidin-4-yl]amino]-2,2-dimethyl-3-oxo-pyrido[3,2-b][1,4]oxazin-4-yl]methyl phosphate hexahydrate

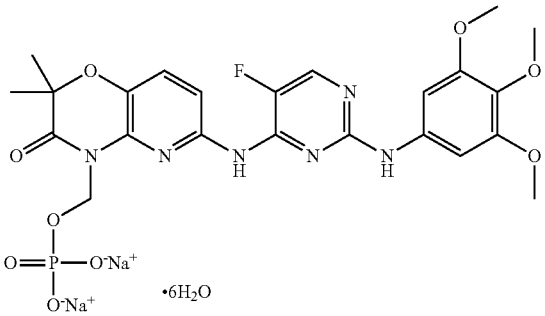

Step A: Preparation of 6-[(2-chloro-5-fluoro-pyrimidin-4-yl)amino]-2,2-dimethyl-4H-pyrido[3,2-b][1,4]oxazin-3-one

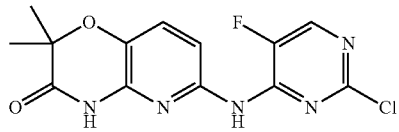 [SMILES: CC1(C)Oc2ccc(Nc3nc(Cl)ncc3F)nc2NC1=O]

5-fluoropyrimidine-2,4-diol (525 kg, 1.00 mol eq) is mixed with phosphorous oxychloride (1545 kg, 2.50 mol eq) and heated to about 100° C. with stirring under a nitrogen atmosphere. N,N-dimethylaniline (980 kg, 2.00 mol eq) is then added over a period of about 9 hours and the resulting mixture stirred at about 100° C. for up to 4 hours. This is then cooled to about 20° C. over about 2 hours and then quenched into a mixture of water (3150 kg) and dichloromethane (1915 kg), maintaining the temperature below 40° C. The contents are then stirred at about 20° C. for at least 3 hours and then the layers separated. The aqueous phase is washed with dichloromethane (1915 kg) and the layers again separated. The combined organics are then washed with concentrated aqueous hydrochloric acid (525 kg) at least once, sometimes more than once, then with 5% w/w aqueous sodium hydrogen carbonate solution (2625 kg). The resulting organic solution is then distilled at atmospheric pressure down to about 1310 kg to give a solution of 2,4-dichloro-5-fluoro-pyrimidine in dichloromethane, with typical solution strength of about 50% w/w and yield of about 95%. This solution is then used directly in the next process.

6-amino-2,2-dimethyl-4H-pyrido[3,2-b][1,4]oxazin-3-one (450 kg, 1.00 mol eq) is stirred in a mixture of methanol (1971 kg) and water (1610 kg) under a nitrogen atmosphere with heating to about 65° C. To this is added a solution of 2,4-dichloro-5-fluoro-pyrimidine in dichloromethane (545 kg 2,4-dichloro-5-fluoro-pyrimidine, 1.40 mol eq, about 50% w/w solution) over a period of about 4 hours, during which dichloromethane is distilled off. The mixture is then stirred at about 70° C. until distillation is complete and then at reflux for about 15 hours. This is then cooled to about 45° C. and filtered. The filtered solid is washed twice with methanol (2×675 kg) and then dried under vacuum at about 55° C. Once dry, the solid is slurried in 85% w/w aqueous formic acid (3150 kg) at about 50° C. for about 6 hours and then filtered. This slurry may be repeated. The resulting damp solid is cooled to about 20° C., washed twice with methanol (2×1800 kg) and dried under vacuum at about 80° C. to give the title compound (577 kg, 77%) as a colored solid.

$^1$H NMR (400 MHz, DMSO-d$_6$) δ ppm 1.42 (s, 6H) 7.41 (d, J=8.5 Hz, 1H) 7.46 (dd, J=8.5, 0.5 Hz, 1H) 8.34 (d, J=3.3 Hz, 1H) 10.10 (br. s, 1H) 11.12 (br. s, 1H).

m/z 324 [MH]$^+$.

Step B: Preparation of 6-[[5-Fluoro-2-(3,4,5-trimethoxyanilino)pyrimidin-4-yl]amino]-2,2-dimethyl-4H-pyrido[3,2-b][1,4]oxazin-3-one

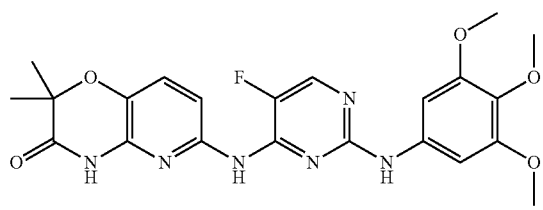

6-[(2-chloro-5-fluoro-pyrimidin-4-yl)amino]-2,2-dimethyl-4H-pyrido[3,2-b][1,4]oxazin-3-one (Step A) (568 kg, 1.00 mol eq) is mixed with 3,4,5-trimethoxyaniline (402 kg, 1.25 mol eq) in N-methylpyrrolidin-2-one (2835 kg) with stirring under a nitrogen atmosphere. To this is added water (11 kg) and the mixture heated to about 120° C. and stirred for about 10 hours. This is then cooled to about 65° C. and the pH adjusted to pH 8.5 with 4% w/w aqueous sodium hydroxide solution. The resulting slurry is further cooled to about 20° C., stirred for at least 6 hours and then filtered. The filtered solid is washed twice with water (2×1440 kg) then twice with acetone (2×1140 kg) and finally dried under vacuum at about 40° C. to give the title compound (754 kg, 91%) as a colored solid.

$^1$H NMR (400 MHz, DMSO-d$_6$) δ ppm 1.42 (s, 6H) 3.59 (s, 3H) 3.66 (s, 6H) 7.04 (s, 2H) 7.32 (d, J=8.5 Hz, 1H) 7.68 (d, J=8.5 Hz, 1H) 8.13 (d, J=3.4 Hz, 1H) 9.10 (br. s, 1H) 9.14 (br. s, 1H) 11.06 (br. s, 1H).

m/z 471 [MH]$^+$.

Step C: Preparation of ditert-butyl [6-[[5-fluoro-2-(3,4,5-trimethoxyanilino)pyrimidin-4-yl]amino]-2,2-dimethyl-3-oxo-pyrido[3,2-b][1,4]oxazin-4-yl]methyl phosphate

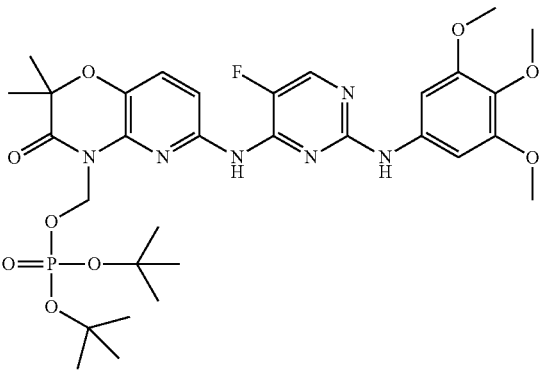

A mixture of 6-[[5-Fluoro-2-(3,4,5-trimethoxyanilino)pyrimidin-4-yl]amino]-2,2-dimethyl-4H-pyrido[3,2-b][1,4]oxazin-3-one (Step B) (382 kg, 1.00 mol eq), tetra-n-butylammonium chloride (57.5 kg, 0.25 mol eq) and potassium carbonate (252 kg, 2.25 mol eq) in N,N-dimethylacetamide (1792 kg) is warmed to about 40° C. with stirring. To this is added a solution of ditert-butyl chloromethyl phosphate (Example 2) in isopropyl acetate (229 kg ditert-butyl chloromethyl phosphate, 1.10 mol eq, about 25% w/v solution). The resulting mixture is stirred for about 8 hours and then cooled to about 5° C. Isopropyl acetate (1329 kg) is added and then water (2292 kg) slowly, maintaining the temperature at <25° C. The layers are then separated, retaining the upper layer of the three observed. To this is added acetic acid (99 kg) and the resulting solution of the sub-title compound is used directly in the next step.

Step D: Preparation of [6-[[5-fluoro-2-(3,4,5-trimethoxyanilino)pyrimidin-4-yl]amino]-2,2-dimethyl-3-oxo-pyrido[3,2-b][1,4]oxazin-4-yl]methyl dihydrogen phosphate; acetic acid solvate

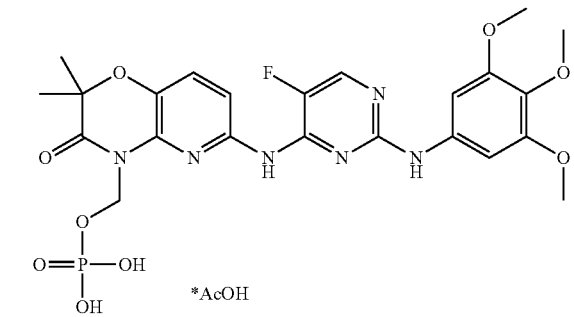

A mixture of acetic acid (2605 kg) and water (860 kg) along with [6-[[5-fluoro-2-(3,4,5-trimethoxyanilino)pyrimidin-4-yl]amino]-2,2-dimethyl-3-oxo-pyrido[3,2-b][1,4]oxazin-4-yl]methyl dihydrogen phosphate; acetic acid solvate seed (synthesised according to the method described in WO 2011/002999) (15 kg, 0.03 mol eq) are heated to about 70° C. To this is then added the solution of ditert-butyl [6-[[5-fluoro-2-(3,4,5-trimethoxyanilino)pyrimidin-4-yl]amino]-2,2-dimethyl-3-oxo-pyrido[3,2-b][1,4]oxazin-4-yl]methyl phosphate (Step C) over about 5 hours. The resulting mixture is further stirred for about 1 hour, cooled to about 50° C. and then filtered, washing twice with acetone (2×605 kg). The damp solid is finally dried under vacuum at about 40° C. to give the sub-title compound (317 kg, 61%) as an off white solid.

$^1$H NMR (400 MHz, DMSO-$d_6$) δ ppm 1.45 (s, 6H) 1.90 (s, 3H) 3.61 (s, 3H) 3.68 (s, 6H) 5.81 (d, J=6.9 Hz, 2H) 7.06 (s, 2H) 7.40 (d, J=8.5 Hz, 1H) 7.95 (d, J=8.5 Hz, 1H) 8.18 (d, J=3.4 Hz, 1H) 9.20 (br. s, 2H).

m/z 581 [MH]$^+$.

Step E: Preparation of [6-[[5-fluoro-2-(3,4,5-trimethoxyanilino)pyrimidin-4-yl]amino]-2,2-dimethyl-3-oxo-pyrido[3,2-b][1,4]oxazin-4-yl]methyl dihydrogen phosphate; N,N-dimethylformamide solvate

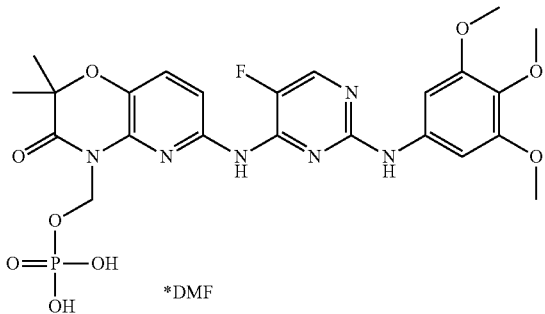

*DMF

To [6-[[5-fluoro-2-(3,4,5-trimethoxyanilino)pyrimidin-4-yl]amino]-2,2-dimethyl-3-oxo-pyrido[3,2-b][1,4]oxazin-4-yl]methyl dihydrogen phosphate; acetic acid solvate (Step D) (3.50 kg) in a heated vessel at about 65° C. is added hot N,N-dimethylformamide (17.5 kg, preheated to about 70° C.). The mixture is stirred at about 65° C. for about 30 minutes, [6-[[5-fluoro-2-(3,4,5-trimethoxyanilino)pyrimidin-4-yl]amino]-2,2-dimethyl-3-oxo-pyrido[3,2-b][1,4]oxazin-4-yl]methyl dihydrogen phosphate; N,N-dimethylformamide solvate seed (synthesised according to the method described in WO 2011/002999) (0.04 kg) is added, and then the mixture is cooled to about 40° C. over about 4 hours. This is then warmed again to about 60° C. over about 1 hour, held for about 30 minutes and then cooled to about 20° C. over about 8 hours. The resulting slurry is stirred for at least 10 hours, filtered and then washed twice with methyl-t-butyl ether (2×7.88 kg). The damp solid is finally dried under vacuum at about 40° C. to give the sub-title compound (2.82 kg, 88%) as a white to off white solid.

$^1$H NMR (400 MHz, DMSO-$d_6$) δ ppm 1.45 (s, 6H) 2.72 (d, J=0.6 Hz, 3H) 2.88 (d, J=0.6 Hz, 3H) 3.61 (s, 3H) 3.68 (s, 6H) 5.81 (d, J=6.9 Hz, 2H) 7.06 (s, 2H) 7.40 (d, J=8.6 Hz, 1H) 7.94-7.96 (m, 2H) 8.18 (d, J=3.4 Hz, 1H) 9.21 (br. s, 2H);

m/z 581 [MH]$^+$.

Step F: Preparation of bis(triethylammonium) [6-[[5-fluoro-2-[(3,4,5-trimethoxyphenyl)amino]pyrimidin-4-yl]amino]-2,2-dimethyl-3-oxo-pyrido[3,2-b][1,4]oxazin-4-yl]methyl phosphate To [6-[[5-fluoro-2-(3,4,5-trimethoxyanilino)pyrimidin-4-yl]amino]-2,2-dimethyl-3-oxo-pyrido[3,2-b][1,4]oxazin-4-yl]methyl dihydrogen phosphate; N,N-dimethylformamide solvate (Step E) (1.00 kg, 1.00 mol eq) is added a solution of triethylamine (0.34 kg, 2.20 mol eq) in isopropanol (1.32 kg) and water (3.33 kg). This is stirred at about 20° C. to give a solution which is then filtered. The resulting solution of the sub-title compound is used directly in the next step.

Step G: Preparation of disodium [6-[[5-fluoro-2-(3,4,5-trimethoxyanilino)pyrimidin-4-yl]amino]-2,2-dimethyl-3-oxo-pyrido[3,2-b][1,4]oxazin-4-yl]methyl phosphate hexahydrate

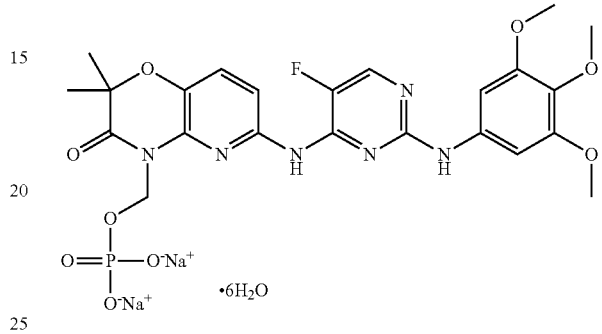

·6H$_2$O

The solution of bis(triethylammonium)[6-[[5-fluoro-2-[(3,4,5-trimethoxyphenyl)amino]pyrimidin-4-yl]amino]-2,2-dimethyl-3-oxo-pyrido[3,2-b][1,4]oxazin-4-yl]methyl phosphate (Step F) is warmed to about 40° C. and then a solution of sodium 2-ethylhexanoate (0.05 kg, 0.20 mol eq) in isopropanol (0.04 kg) and water (0.10 kg) is added over about 20 minutes. To the resulting solution is then added disodium [6-[[5-fluoro-2-(3,4,5-trimethoxyanilino)pyrimidin-4-yl]amino]-2,2-dimethyl-3-oxo-pyrido[3,2-b][1,4]oxazin-4-yl]methyl phosphate hexahydrate seed (synthesised according to the method described in WO 2011/002999)(0.01 kg, 0.01 mol eq) and the mixture is held for about 3.5 hours. A solution of sodium 2-ethylhexanoate (0.97 kg, 3.80 mol eq) in isopropanol (0.75 kg) and water (1.90 kg) is next added over about 6 hours. The resulting slurry is cooled to about 20° C. over at least 1 hour, stirred for about 1 hour and then filtered, washing with a mixture of isopropanol (0.53 kg) and water (1.33 kg) and then with acetone (1.58 kg). The damp solid is finally dried under vacuum (about 400 mbar) at about 40° C. to give the title compound (1.03 kg, 92%) as a white to off white solid.

$^1$H NMR (500 MHz, Methanol-$d_4$) δ ppm 1.52 (s, 6H) 3.78 (s, 3H) 3.80 (s, 6H) 5.86 (d, J=4.9 Hz, 2H) 6.97 (s, 2H) 7.24 (d, J=8.6 Hz, 1H) 8.00 (d, J=3.6 Hz, 1H) 8.10 (d, J=8.6 Hz, 1H);

m/z 581 [MH]$^+$.

Example 2

Preparation of Ditert-Butyl Chloromethyl Phosphate

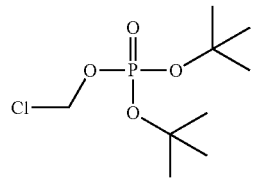

To a mixture of potassium ditert-butyl phosphate (261 kg, 1.00 mol eq), tetra-n-butylammonium hydrogensulphate (18.5 kg, 0.05 mol eq) and sodium hydrogencarbonate (400 kg, 4.50 mol eq) in water (1150 kg) is added isopropyl acetate (1275 kg). The mixture is warmed to about 35° C. and then to this is added chloromethylchlorosulphate (313 kg, 1.80 mol eq) over about 4 hours. The mixture is further stirred for about 45 minutes, cooled to about 25° C. and then the layers separated. The organic phase is cooled to about 10° C. and washed twice with 2% w/v aqueous potassium hydrogencarbonate solution (2×800 kg) and then with a mixed 2% w/v potassium hydrogencarbonate and 20% w/v potassium hydrogencarbonate aqueous solution (640 kg). The resulting organic solution is then distilled at <100 mbar to half volume, maintaining the temperature below 45° C. The resulting mixture is filtered, washing the filter with isopropyl acetate (115 kg), to give the title compound as a solution, with typical solution strength of about 25% w/v and yield of about 90%. This solution is then used directly in Example 1, Step C.

We claim:

1. A process for preparing a compound of formula (I) or hydrate thereof:

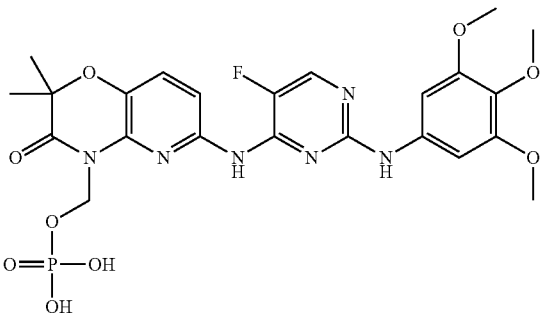

comprising:
a) contacting an amide solvate of the compound of formula (II):

(II)

with an amine to form an amine salt of the compound of formula (II); and
b) contacting the amine salt with a reagent comprising sodium ions to form the compound of formula (I) or hydrate thereof.

2. The process according to claim 1, wherein the compound of formula (I) is in the form of a hexahydrate.

3. A process for preparing a compound of formula (VI):

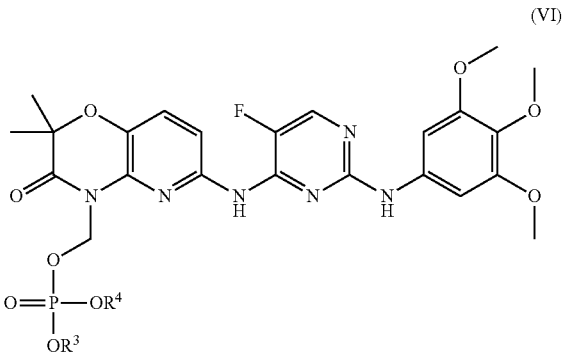

comprising contacting a compound of formula (VII):

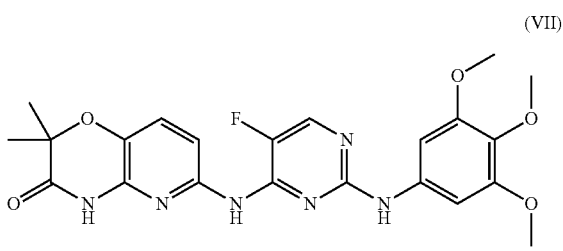

with a compound of formula (VIII):

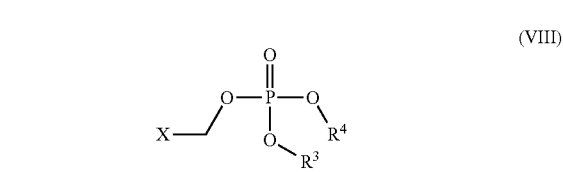

in the presence of a tetra-alkylammonium salt,
wherein:
$R^3$ and $R^4$ are each independently $C_{1-6}$ alkyl; and
X is halogen;
to form a compound of formula (VI).

4. A process for preparing a compound of formula (I) or hydrate thereof comprising:

(I)

(a) contacting a compound of formula (VI):

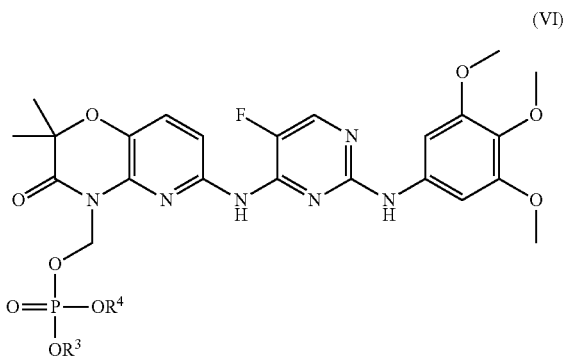

wherein $R^3$ and $R^4$ are each independently $C_{1-6}$ alkyl; with acetic acid and water to form the compound of formula (V):

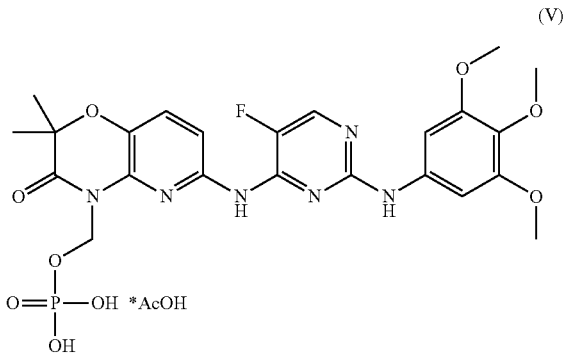

(b) contacting the compound of formula (V) with an amide to form an amide solvate of the compound of formula (II):

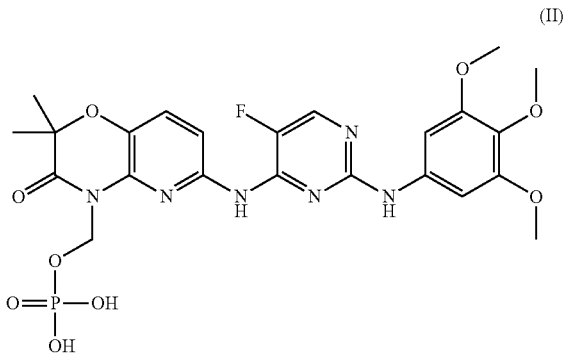

(c) contacting the amide solvate of the compound of formula (II) with an amine to form an amine salt of the compound of formula (II); and (d) contacting the amine salt of the compound of formula (II) with a reagent comprising sodium ions to form the compound of formula (I) or hydrate thereof.

5. The process according to claim 4, wherein the compound of formula (I) is in the form of a hexahydrate.

6. The process according to claim 1, wherein the amide component of the amide solvate is N,N-dimethylformamide (DMF).

7. The process according to claim 1, wherein the amine component of the amine salt of the compound of formula (II) is $N(R^{40})_3$, where each $R^{40}$ is independently —H or $C_{1-12}$alkyl, or two $R^{40}$ groups together with the nitrogen to which they are attached form a 4 to 6-membered heterocyclic ring and the remaining $R^{40}$ is —H or $C_{1-12}$alkyl.

8. The process according to claim 1, wherein the amine component of the amine salt of the compound of formula (II) is triethylamine.

9. The process according to claim 1, wherein the reagent comprising sodium ions is sodium 2-ethylhexanoate.

10. The process according to any claim 2, wherein the amide component of the amide solvate is N,N-dimethylformamide (DMF).

11. The process according to claim 2, wherein the amine component of the amine salt of the compound of formula (II) is $N(R^{40})_3$, where each $R^{40}$ is independently —H or $C_{1-12}$alkyl, or two $R^{40}$ groups together with the nitrogen to which they are attached form a 4 to 6-membered heterocyclic ring and the remaining $R^{40}$ is —H or $C_{1-12}$alkyl.

12. The process according to claim 2, wherein the amine component of the amine salt of the compound of formula (II) is triethylamine.

13. The process according to claim 2, wherein the reagent comprising sodium ions is sodium 2-ethylhexanoate.

14. The process according to any claim 7, wherein the amide component of the amide solvate is N,N-dimethylformamide (DMF).

15. The process according to claim 7, wherein the amine component of the amine salt of the compound of formula (II) is $N(R^{40})_3$, where each $R^{40}$ is independently —H or $C_{1-12}$alkyl, or two $R^{40}$ groups together with the nitrogen to which they are attached form a 4 to 6-membered heterocyclic ring and the remaining $R^{40}$ is —H or $C_{1-12}$alkyl.

16. The process according to claim 7, wherein the amine component of the amine salt of the compound of formula (II) is triethylamine.

17. The process according to claim 7, wherein the reagent comprising sodium ions is sodium 2-ethylhexanoate.

* * * * *